(12) United States Patent
Drake, Jr.

(10) Patent No.: US 7,612,890 B2
(45) Date of Patent: Nov. 3, 2009

(54) SYSTEM AND METHOD FOR CONTROLLING WAFER TEMPERATURE

(75) Inventor: Thomas E. Drake, Jr., Ft. Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 297 days.

(21) Appl. No.: 10/142,178

(22) Filed: May 9, 2002

(65) Prior Publication Data

US 2002/0171845 A1 Nov. 21, 2002

Related U.S. Application Data

(63) Continuation-in-part of application No. 09/416,399, filed on Oct. 12, 1999, now Pat. No. 6,657,733.

(60) Provisional application No. 60/091,229, filed on Jun. 30, 1998.

(51) Int. Cl.
G01B 9/02 (2006.01)

(52) U.S. Cl. .................................................. 356/502

(58) Field of Classification Search ................. 356/502, 356/432
See application file for complete search history.

(56) References Cited

U.S. PATENT DOCUMENTS

| | | | | |
|---|---|---|---|---|
| 3,911,733 A | 10/1975 | Bhuta et al. | ................. | 73/88 |
| 3,992,627 A | 11/1976 | Stewart | ................. | 250/312 |
| 4,349,112 A | 9/1982 | Wilks et al. | ................. | 209/538 |
| 4,355,538 A | 10/1982 | Hall | ................. | 73/811 |
| 4,381,676 A | 5/1983 | Kaule et al. | ................. | 73/657 |
| 4,422,177 A | 12/1983 | Mastronardi et al. | ................. | 378/17 |
| 4,521,118 A | 6/1985 | Rosencwaig | ................. | 374/5 |
| 4,581,939 A | 4/1986 | Takahashi | ................. | 73/643 |
| 4,636,088 A | 1/1987 | Rosencwaig et al. | ................. | 374/5 |
| 4,650,346 A | 3/1987 | Tehon | ................. | 374/117 |
| 4,803,639 A | 2/1989 | Steele et al. | ................. | 364/507 |
| 4,809,308 A | 2/1989 | Adams et al. | ................. | 378/99 |
| 4,841,460 A | 6/1989 | Dewar et al. | ................. | 364/571.02 |
| 5,014,293 A | 5/1991 | Boyd et al. | ................. | 378/197 |
| 5,065,630 A | 11/1991 | Hadcock et al. | ................. | 73/802 |
| 5,113,079 A | 5/1992 | Matulka | ................. | 250/550 |
| 5,119,408 A | 6/1992 | Little et al. | ................. | 378/4 |

(Continued)

FOREIGN PATENT DOCUMENTS

EP 0 339 625 A1 11/1989

(Continued)

OTHER PUBLICATIONS

NTIAC Newsletter; vol. 27, No. 5, Sep. 2002, 5 pp.

(Continued)

*Primary Examiner*—Hwa S Lee (Andrew)
(74) *Attorney, Agent, or Firm*—Bracewell & Giuliani LLP (57) ABSTRACT

The invention is directed to a system and method for implementing process control for temperature of a semiconductor wafer using sonic NDE techniques. The system may, for example, generate ultrasound waves in a test object during the manufacturing process. A detector such as an interferometer may be used to detect the ultrasound waves. An interpreter or analyzer may determine the temperature of the semiconductor wafer from the waves. Then, a control system may determine and implement an appropriate control action on the process.

13 Claims, 5 Drawing Sheets

U.S. PATENT DOCUMENTS

| | | | |
|---|---|---|---|
| 5,122,672 A | 6/1992 | Mansour | 250/571 |
| 5,131,748 A | 7/1992 | Monchalin et al. | 356/349 |
| 5,140,533 A | 8/1992 | Celette | 364/559 |
| 5,295,073 A | 3/1994 | Celette | 364/424 |
| 5,310,260 A * | 5/1994 | Schietinger et al. | 374/142 |
| 5,319,567 A | 6/1994 | Ebenstein | 364/474.34 |
| 5,384,717 A | 1/1995 | Ebenstein | 364/560 |
| 5,402,233 A * | 3/1995 | Schultz et al. | 356/493 |
| 5,442,572 A | 8/1995 | Kiridena et al. | 364/560 |
| 5,490,195 A | 2/1996 | Berkley | 378/72 |
| 5,541,856 A | 7/1996 | Hammermeister | 364/552 |
| 5,552,984 A | 9/1996 | Crandall et al. | 364/424.03 |
| 5,574,226 A | 11/1996 | Reuther et al. | 73/669 |
| 5,604,592 A * | 2/1997 | Kotidis et al. | 356/493 |
| 5,608,166 A | 3/1997 | Monchalin et al. | 73/657 |
| 5,637,812 A | 6/1997 | Baker et al. | 73/865.6 |
| 5,724,138 A * | 3/1998 | Reich et al. | 356/492 |
| 5,848,115 A | 12/1998 | Little et al. | 378/4 |
| 5,900,937 A * | 5/1999 | Wang | 356/511 |
| 6,016,202 A * | 1/2000 | Fuchs et al. | 356/432 |
| 6,023,985 A | 2/2000 | Fournier | 73/865.6 |
| 6,047,041 A | 4/2000 | Ellinger | 378/58 |
| 6,057,927 A * | 5/2000 | Levesque et al. | 356/432 |
| 6,181,431 B1 * | 1/2001 | Siu | 356/502 |
| 6,188,050 B1 | 2/2001 | Duffer et al. | 219/497 |
| 6,205,240 B1 | 3/2001 | Pietrzak et al. | 382/152 |
| 6,220,099 B1 | 4/2001 | Marti et al. | 73/633 |
| 6,360,621 B1 | 3/2002 | Eldred et al. | 73/865.6 |
| 6,378,387 B1 | 4/2002 | Froom | 73/865.8 |
| 6,466,643 B1 | 10/2002 | Bueno et al. | 378/58 |
| 6,571,008 B1 | 5/2003 | Bandyopadhyay et al. | 382/154 |
| 6,637,266 B1 | 10/2003 | Froom | 73/583 |

FOREIGN PATENT DOCUMENTS

WO      WO 01/27606 A1      4/2001

OTHER PUBLICATIONS

Froom, Douglas A., et al.; Solving Problems with Advanced Technology, 1999 IEEE, 4 pp.

Alkire, M.G., Department of the Air Force Memo regarding Construction Project Data; May 7, 1982, Bates 000010 through Bates 000068.

U.S. Air Force, Military Construction Project Data, Apr. 14, 1982, Bates 000074 though Bates 000129.

U.S. Air Force, Attachment I to Request for Environmental Impact Analysis, Dec. 2, 1982, Bates 000130 through Bates 000167.

Stanghellini, Frank D., Department of the Air Force Memo regarding Criteria Changes, Jan. 9, 1985, Bates 000168 through Bates 000214.

Metro Today, The Sacramento Union; May 12, 1983, Bates 000215 through Bates 000216.

Letter Contract Between Department of the Air Force and Par Systems Corp., Aug. 3, 1984, Bates 000217 through Bates 000312.

Timeline and Equipment List for Contract Between Department of the Air Force and Par Systems Corp., Aug. 3, 1984, Bates 000313 through Bates 000325.

Spacemaker, Jun. 19, 1997, Bates 000326 through 000327.

Civilian Personnel Position Description, Department of the Air Force; Jul. 10, 1989, Bates 000328 through Bates 000332.

Aviation Week & Space Technology, Mar. 13, 1989, Bates 000333 through Bates 000336.

UltraOptec, Laser Ultrasonic System, 1999 IEEE, Bates 000337 through Bates 000340.

J.W. Bader, et al., Laser Ultrasonics or Alternative NDI Composite Defect, Nov. 20, 1990, Bates 000342 through Bates 000446.

Douglas A. Froom, Statement of Work for Advanced Ultrasonic Component Inspection System, Jul. 14, 1993, Bates 000447 through 000490.

Award of Contract from Department of the Air Force, Aug. 11, 1993, Bates 000491 through Bates 000492.

UltraOptec, LUIS Phase 3 Acceptance Test Report, Feb. 16, 1996, Bates 000493 through Bates 000501.

* cited by examiner

SYSTEM AND METHOD FOR CONTROLLING WAFER TEMPERATURE

RELATED APPLICATIONS

This application claims the benefit of, incorporates by reference, and is a Continuation-In-Part of Non-Provisional patent application Ser. No. 09/416,399 filed on Oct. 12, 1999, now U.S. Pat. No. 6,657,733 entitled "METHOD AND APPARATUS FOR DETECTING ULTRASONIC SURFACE DISPLACEMENTS USING POST COLLECTION OPTICAL AMPLIFICATION" to Thomas E. Drake. Non-Provisional patent application Ser. No. 09/416,399 in turn claims benefit to U.S. Provisional Application No. 60/091,229 filed on Jun. 30, 1998. This application incorporates by reference the prior U.S. Provisional Application No. 60/091,240 filed on Jun. 30, 1998 entitled "METHOD AND APPARATUS FOR ULTRASONIC LASER TESTING" to Thomas E. Drake. This application is related to and incorporates by reference: Non-Provisional patent application Ser. No. 10/142,073, filed on May 9, 2002, entitled "SYSTEM AND METHOD FOR CONTROLLING TUBE THICKNESS" to Thomas E. Drake; Non-Provisional patent application Ser. No. 10/142,072, filed on May 9, 2002, entitled "SYSTEM AND METHOD FOR ON-LINE CONTROL OF PAPER ELASTICITY AND THICKNESS" to Thomas E. Drake; and Non-Provisional patent application Ser. No. 10/142,071, filed on May 9, 2002, entitled "SYSTEM AND METHOD FOR CONTROL OF PAINT THICKNESS" to Thomas E. Drake.

TECHNICAL FIELD OF THE INVENTION

This invention relates in general to non-destructive examination techniques. More specifically, the invention relates to control using ultrasound testing methods for determining the temperature of a semiconductor wafer.

BACKGROUND OF THE INVENTION

Semiconductor processing requires close temperature control for high temperature processes. High temperatures are used in various steps in semiconductor manufacturing including Rapid Thermal Processing, epilayer growth, structure processing, and bum-in, among others. Poor temperature control could lead to off-spec layer thickness, diffuse doping, and structural flaws, among others. In general, poor temperature control may lead to low yield.

However, typical measuring techniques are invasive, slow, and difficult to interpret. Thermocouples do not respond fast enough to be used in rapid thermal processing. Further, they must be located in the chamber and on the wafer.

Optical pyrometers are based on the thermal radiation of the wafer. The thermal radiation is strongly affected by the emissivity of the wafer. The emissivity of the wafer is a function of film depositions, backside roughness, doping levels, and temperature, among others. The pyrometers may also be affected by heat lamp radiation.

In addition, other acoustic techniques require contact with the wafer and must be located in the chamber. They are invasive and require contact.

As such, these techniques are not suitable for use in process control. The slow testing time may not provide enough information for process control applications. Further, a lack of automation in the analyzing the results limits applicability to process control. In addition, contact with the part may not be suitable, preventing the technique from use in the process.

As such, many typical NDE techniques suffer from deficiencies in speed and automation. Many other problems and disadvantages of the prior art will become apparent to one skilled in the art after comparing such prior art with the present invention as described herein.

SUMMARY OF THE INVENTION

Aspects of the invention may be found in an apparatus for determining the temperature of a semiconductor wafer. The apparatus may have a sonic energy generator, one or more detectors and an interpreter. The sonic energy generator may, for example, be a laser generator directing a beam of coherent electromagnetic energy at an object. From the impinging energy, sonic energy waves may be generated about the object or along the surface of the object, among others. The one or more detectors may detect and/or measure the sonic energy waves. An interpreter may then be used to determine the temperature of a semiconductor wafer.

Aspects of the invention may also be found in a method for determining the temperature of a semiconductor wafer. Sonic energy waves may be generated about a test object using a sonic energy generator. The sonic energy waves may be detected and/or measured by a sonic energy detector. The temperature may be determined by an interpreter. For example, the interpreter may correlate sonic velocity with temperature.

Another aspects of the invention may be found in an apparatus for process control of the temperature of a semiconductor wafer. The apparatus may have a sonic energy generator, one or more detectors, and a control system. The sonic energy generator may, for example, be a laser generator directing a beam of coherent electromagnetic energy at an object. From the impinging energy, sonic energy waves may be generated about the object or along the surface of the object, among others. The one or more detectors may detect and/or measure the sonic energy waves. The control system may determine what action may be taken to achieve and/or maintain an aspect of the object near or about a set point.

A further aspect of the invention may be found in a method for process control of the temperature of a semiconductor wafer. Sonic energy waves may be generated about a test object using a sonic energy generator. The sonic energy waves may be detected and/or measured by a sonic energy detector. An action may be determined, which may achieve and/or maintain an aspect of the object near or about a set point.

Another aspects of the invention may be found in a control system. The control system may have an analyzer, a controller, and interfaces. An interface may receive data from a sonic energy detector. The analyzer may determine and/or generate a signal relating to the temperature. The controller may use the signal from the analyzer to determine an appropriate control action. The action may be implemented using an interface to the process. Furthermore, the control system may have one or more modelers, one or more stored results, one or more threshold values, and one or more algorithms. Each of these may or may not be used by the analyzer or controller in performing their respective function.

As such, a system for control of a semiconductor manufacturing process is described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and advantages thereof, reference is now made to the following description taken in conjunction with the accompanying drawings in which like reference numbers indicate like features and wherein.

Corresponding reference numerals indicate corresponding parts throughout the several views of the drawings.

DETAILED DESCRIPTION OF THE PREFERRED EMBODIMENT

Sonic energy traverses through objects with varying characteristics. These characteristics may include speed, wave type, frequency spectrum, and amplitude. Further the sonic energy may partially reflect from surfaces or inconsistencies. Waves may also translate across a surface.

The characteristics of the sonic energy may be a function of various aspects of the substance about which the sonic energy travels. These aspects may include elasticity, internal structure, flaws, thickness of material, and layers of film, among others. These aspects may be a further function of temperature. As such, sonic energy waves may be used to aid in determining aspects of the material for use in process control.

For example, the velocity of a sonic energy signal may be measured and correlated with temperature. In this manner, the temperature of a semiconductor wafer may be controlled by measuring the sonic energy signal, determining the temperature, and determining a control action. The control action may be varying a parameter associated with a heat lamp, heating element, plasma source, pressure, laser, and/or sonic device, among others.

Figure 1:
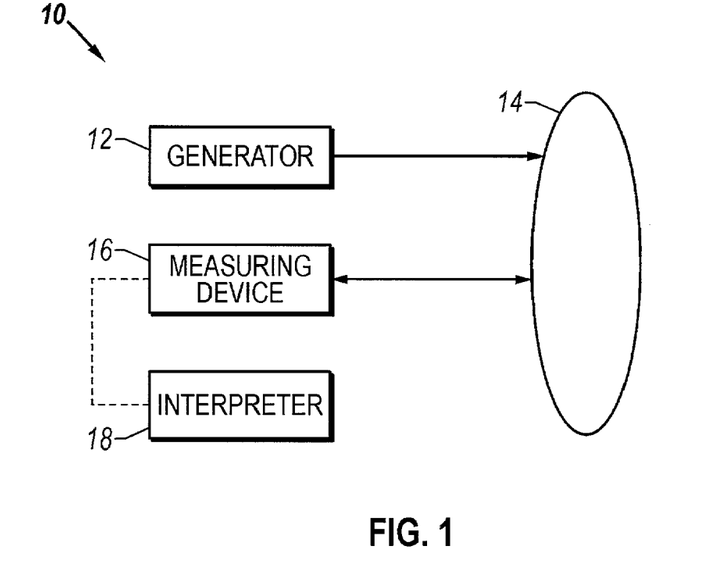
FIG. 1 is a schematic block diagram the system, according to the invention.

FIG. 1 depicts a system, according to the invention. In the system 10, a sonic energy generator 12 may generate sonic energy waves in a test object 14. The system may also have a detector or measuring device 16. The detector or measuring device 16 may detect or measure the sonic energy waves. An interpreter 18 may be used to determine the sonic wave characteristic, material aspect and/or value of a variable from which the material aspect depends.

The sonic energy generator 12 may take various forms. These forms may include a coherent electromagnetic energy source, a laser, a plasma generator, and a transducer, among others. Further, the coherent electromagnetic energy source and/or laser may take various forms. These forms may include a $CO_2$ laser, a q-switch YAG laser, a mid-IR laser, and other solid-state and/or gas lasers, among others. However, various lasers may be envisaged.

The measuring device 16 may take various forms. These forms may include an interferometer, a gas-coupled laser acoustic detector, and a transducer, among others. Further, the interferometer may take the form of a Mach-Zender, Fabry-Perot, Dual Differential Confocal Fabry-Perot, Two Wave Mixing, photorefractive or other interferometer. Other interferometers and sonic energy detection methods may be used as well. A laser may be used to generate coherent electromagnetic energy for use in the interferometer. One exemplary embodiment is a long pulse ND:YAG laser. However, other lasers may be used.

The interpreter 18 may take various forms. These forms may include a computer, workstation, handheld, computational circuitry, analog device, or digital alarm, among others. Further, the interpreter may compare the signal to an expected signal, determine the location of one or more peaks, determine the amplitude of one or more peaks, and transform the signal, among others. The interpreter may operate on the signal in a time domain or frequency domain, among others. Further, the interpreter may determine the velocity of a sonic energy signal and/or, from the velocity, determine temperature.

In one exemplary embodiment, the system may take the form of a laser ultrasound system. The laser ultrasound system may use a $CO_2$ laser. A beam from the laser may be direct to the object. This beam may be directed through fiber optic cable. A ND:YAG laser may direct a beam of coherent electromagnetic energy toward the object. The beam may, at least in part, reflect from the object with an altered characteristic indicative of the sonic energy. Part of the reflected beam may be collected by the collection optics of a dual differential confocal Fabry-Perot interferometer. However, a photorefractive, two wave mixing, or other interferometer may be used.

In this exemplary embodiment, the interferometer may generate a signal. The signal may be interpreted by the interpreter or analyzer. From the signal, the interpreter or analyzer may determine the velocity of a sonic energy signal and from the velocity determine temperature. However, various other characteristic of the sonic energy signal may be used in determining temperature.

Figure 2:
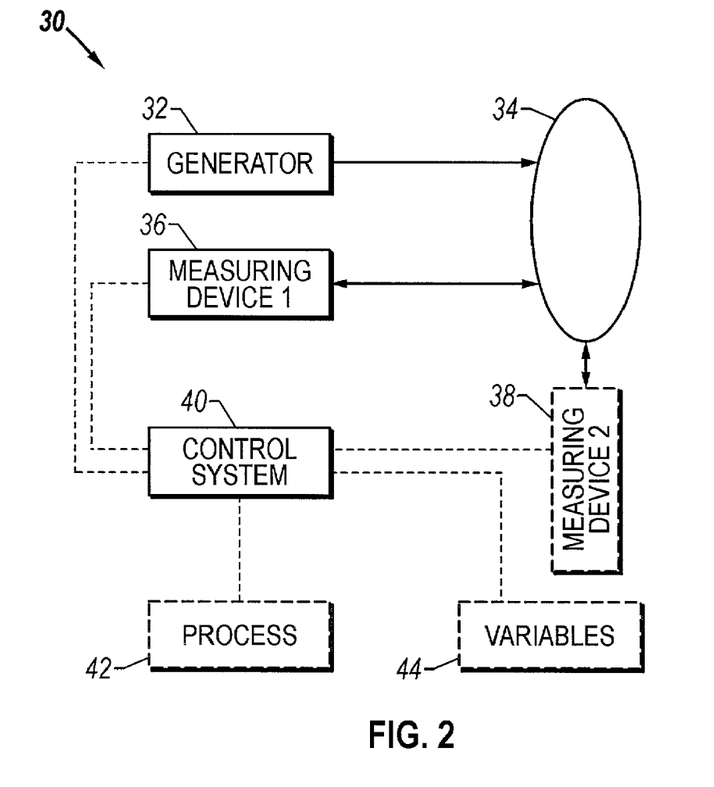
FIG. 2 is a schematic block diagram of the system, according to the invention.

FIG. 2 is a schematic block diagram of a system, according to the invention. The system 30 may have a generator 32, one or more measuring devices 36 and 38, and a control system 40. The control system 40 may or may not be coupled to generator 32 and the one or more measuring devices 36 and 38. The system 30 may or may not also be coupled to the process 42 and other variables 44. However, various configurations may be envisaged. These elements may be together, separate, or in various combinations, among others.

The generator 32 may generate sonic energy waves in the object 34. The one or more detectors 36 and 38 may detect the sonic energy waves. The control system 40 may receive signals from the one or more detectors 36 and 38. From the signals, the control system 40 may determine an appropriate control action. Further, the control system 40 may implement the control action. The control action may include manipulating characteristics associated with the generator, altering characteristics associated with the measuring device, and manipulating process parameters, among others. The control system may also use other process measurements, parameters, and variables 44 in determining the control action.

The generator 32 may take various forms. These forms may include a coherent electromagnetic energy source, a laser, a plasma generator, and a transducer, among others. Further, the coherent electromagnetic energy source and/or laser may take various forms. These forms may include a $CO_2$ laser, a q-switch YAG laser, a mid-IR laser, and other solid-state and/or gas lasers, among others. However, various lasers may be envisaged.

The one or more measuring devices 36 and 38 may take various forms. These forms may include an interferometer, a gas-coupled laser acoustic detector, and a transducer, among others. Further, the interferometer may take the form of a Fabry-Perot, Dual Differential Confocal Fabry-Perot, Two Wave Mixing, photorefractive or other interferometer. Other interferometers and sonic energy detection methods may be used as well. A laser may be used to generate coherent electromagnetic energy for use in the interferometer. One exemplary embodiment is a long pulse ND:YAG laser. However, other lasers may be used.

The control system 40 may take various forms. These forms may include digital control, analog control, or distributed control system, among others. Further, the control system 40 may or may not be implemented on a computational circuitry, computer, or workstation, among others.

The variables 44 may take various forms. These forms may include known process parameters, other measured values, control parameters, model parameters, algorithm parameters, and set points, among others.

For example, the generator 32 may generate a laser beam. The beam may be directed to a surface of a semiconductor wafer. The beam may impart energy on or about the wafer, generating an ultrasonic signal. The ultrasonic signal may travel about the wafer. A measuring device such as a laser ultrasound system may direct a measuring beam at the surface of the wafer. The beam may be directed to the same or different location as the impinging generating beam. The measuring beam may reflect from the surface with a modulation characteristic of the ultrasonic signal. An interferometer may collect and generate a signal associated with the ultrasonic signal.

The ultrasonic signal may be directed to a control system. The control system may analyze the signal and determine a parameter associated with the temperature of the wafer. For example, the control system may determine a velocity of the ultrasonic wave. Using a correlation between velocity and temperature, the control system may determine the temperature or a parameter indicative of enthalpy. The control system may then use the parameter in determining a control action. The control action may take various forms. These forms may include varying a voltage, current, and/or power provided to a heat lamp or element. Alternately, the control action may be to alter the behavior of a plasma generator, pressure, input temperature, set point on another controller, generator laser, or measuring laser, among others.

Further, more than one measuring device may be used. For example, a second measuring laser and interferometer may be used. This second measuring laser may direct a beam to the same location as the impinging generator beam, the same location as the first measuring beam, or another location, among others. The second measuring device may be on the same side of the wafer or the opposite side, among others. Additionally, the second measuring device may direct a beam at the same angle relative to the surface of the wafer as the first measuring device, or another angle, among others. However, various configurations may be envisaged. Further, these elements may be together, separate, or in various combinations, among others.

Figure 3:
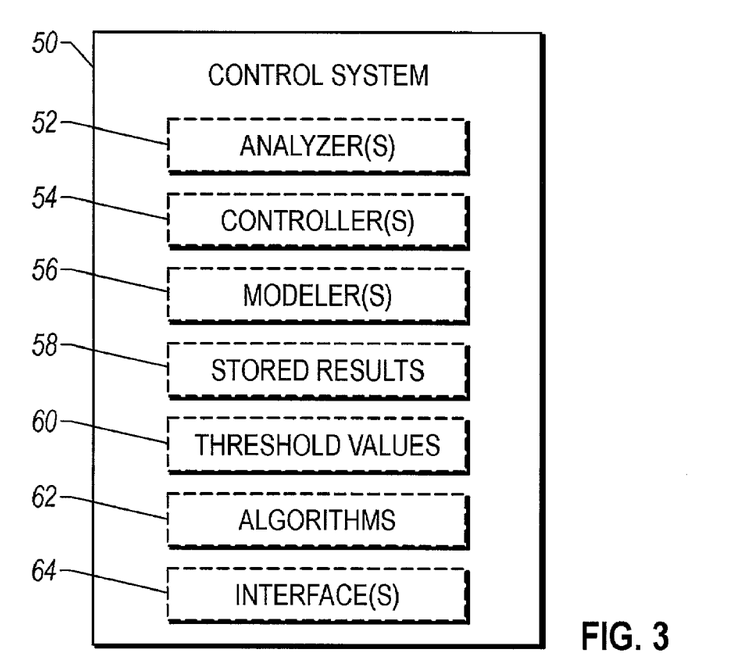
FIG. 3 is a block schematic diagram of an exemplary embodiment of a control system as seen in FIG. 2.

FIG. 3 is a block diagram of an exemplary embodiment of a control system for use in the system as seen in FIG. 2. The control system 50 may have analyzers 52, controllers 54, modelers 56, stored results 58, threshold values 60, algorithms 62, and interfaces 64. However, the control system may have some, all, or none of these elements. Further, these elements may be separate, together, or in various combinations, among others.

The analyzer 52 may perform various functions. These functions may include estimating parameters, determining location and/or amplitude of peaks, comparing location and/or amplitude of peaks to a value, and/or comparing the signals to expected signals. Further the analyzer 52 may perform these functions in time domain and/or frequency domain. In addition, the analyzer may utilize the output of the process, other variables, the modeler 56, stored results 58, and threshold values 60, among others.

The controller 54 may perform various functions. These functions may include determining an action in response to an output from the analyzer 52. The action may relate to manipulating process parameters, generator parameters, measuring device parameters, and other variables, among others. Further, the action may be an alert or message, among others. In addition, the controller 54 may utilize values of process and other variables in determining a control action.

The modeler 56 may take various forms. These forms may include a CAD model, a propagation model, and a control model, among others. Further, the model may use parameters and other outputs from the process, other variables, stored results, threshold values, process setting, and set points, among others, in performing its function. In addition, the model may interact with the controller 54 and/or the analyzer 52, to aid in the function of those units.

The stored results 58 may take various forms. These forms may include previous results, process data, expected results, modeler 56 output, analyzer 52 output, controller 54 output, and user data, among others. The stored results may or may not be accessed by the process, controller 54, analyzer 52, and modeler 60, among others.

The threshold values 60 may be used in various manners. These manners may include for comparison with peaks, set points, model output, process parameters, and other variables, among others. Further, these threshold values 60 may be determined automatically or set by a user.

The algorithms 62 may direct the performance of various functions. These functions may include controller, generator, measuring device, and process functionality, among others.

The interfaces 64 may communicate with various devices. These devices may include the process, generator, measuring devices, other equipment, network interfaces and user interfaces, among others.

For example, the control system may receive a signal indicative of a sonic energy signal. The sonic energy signal may be indicative of the temperature of a semiconductor wafer. The analyzer may determine the velocity of the sonic energy signal by comparing the time domain location of a peak to an expected value. From the velocity, the analyzer may determine temperature. Alternately, the analyzer may regress a parameter associated with temperature by utilizing a propagation model. However, various methods may be envisaged.

A controller may utilize the output of the analyzer to determine an action. For example, the controller may use a PID loop to determine a change in a manipulated variable. The manipulated variable may, for example, be associated with the power provided to a lamp. However, various control actions may be envisaged. Alternately, the controller may use a model in a model predictive algorithm for projecting the consequences of a control action. The controller may then implement an optimal control action.

Figure 4:
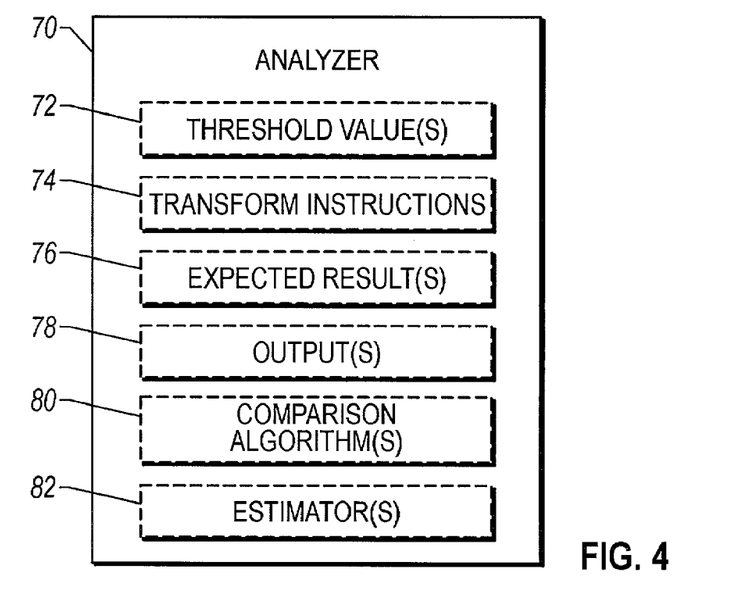
FIG. 4 is a block schematic diagram of an exemplary embodiment of an analyzer as seen in FIG. 3.

FIG. 4 is a block diagram of an exemplary embodiment of an analyzer for use in the controller of FIG. 3. Further, the analyzer may act as an interpreter as seen in FIG. 1. The analyzer 70 may or may not have threshold values 72, transform instructions 74, expected results 76, outputs 78, comparison algorithms 80, and estimators 82. However, the analyzer 70 may have all, some, or none of the elements. Further, these elements may be separate, together, or in various combinations, among others.

The analyzer may receive data from other components in the control system, the measuring devices, process, or other variables, among others. The analyzer may function to analyze these signals together, separately, or in various combinations.

The transform instructions 74 may direct the implementation of various functions. These forms may include scaling and Fourier transforms, among others.

The expected results 76 may take various forms. These forms may include an expected time domain sonic wave, a frequency domain sonic wave response, a location of one or more peaks in a time domain and/or frequency domain data, an amplitude of one or more peaks in a time domain and/or frequency domain data, the output of a wave propagation model, a past result, and expected parameters of a model, among others. However, other expected results may be envisaged.

The comparison algorithms may implement various functions. These functions may include comparison between the signal and an expected result or threshold values. The comparison may be performed in a frequency and/or time domain, among others. Further, these functions may include comparing peak amplitudes with an expected amplitude or threshold value, subtracting an expected result from a signal, and compare a parameter determined by the estimator 82 to a threshold or expected value, among others.

The estimator 82 may function to determine parameters associated with the data from the one or more measuring devices. For example, the estimator 82 may fit a line or some other curve to the data. The estimator 82 may, alternately, regress parameters of a model from the data. Further, the estimator 82 may use various methods and algorithms for fitting and/or regressing. Further, the estimator 82 may use signals and inputs from the control system, process, measuring devices, generator, and other variables, among others, in regressing the parameters.

The outputs 78 may be outputs to other components of the control system. For example, the outputs may direct the results of the comparison algorithms 80, estimators 82, or transform instructions 74, among others, to other components of the control system such as the modeler, controller, interfaces, stored results, or other analyzers, among others.

For example, the analyzer 70 may receive a signal associated with a sonic energy signal. A characteristic of the sonic energy signal may be associated with the temperature of a wafer. The analyzer may determine the characteristic of the sonic energy signal. For example, the characteristic may be velocity. The analyzer may determine the velocity of the sonic energy signal by comparing the location of one or more peaks on a time domain. The analyzer may then determine temperature using a correlation or model. Alternately, the analyzer may regress a parameter associated with temperature from the data and a wave propagation model. However, various characteristics and methods may be envisaged.

Figure 5:
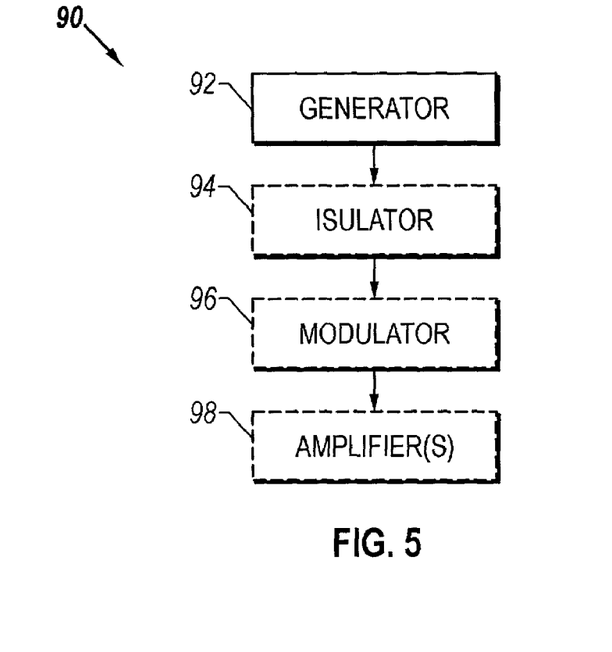
FIG. 5 is a schematic block diagram of an exemplary embodiment of the generator as seen in FIG. 1.

FIG. 5 is a schematic block diagram of an exemplary embodiment of a laser as seen in FIG. 1 and FIG. 2. The laser 90 may be used as a sonic energy generator or a beam generator for an interferometer, among others. The laser 90 may, for example, have a pulse generator 92 that generates a pulse. The pulse may traverse an isolator 94, a modulator 96, and one or more amplifiers 98. However, these elements may or may not be included. Further, these elements may be separate, together, or in any combination, among others.

The pulse generator 92 may take various forms. The isolator 94 may function to prevent backscattering of light into the pulse generator.

The modulator 96 may take various forms. These forms may include electro-optic modulators, and acousto-optic modulators, among others. Further, the modulator 96 may function to alter wave characteristics such as pulse length, pulse frequency profile, phase and pulse amplitude, among others. This function may or may not be implemented in conjunction with the amplifiers 98.

The amplifiers 98 may take various forms. These forms may include pumped slabs, cylinders, and zigzag slabs, among others. The amplifiers may function to increase the amplitude of the laser pulse. In addition, the amplifiers may be configured to alter other wave characteristics such as frequency profile, and pulse length, among others.

For example, a modulator may be used to narrow the band width of a generating beam. Alternately, the frequency of the generating beam may be adjusted to compensate for attenuation in the wafer. Further, a controller may manipulate the character of the generating beam in response to measurements.

Figure 6:
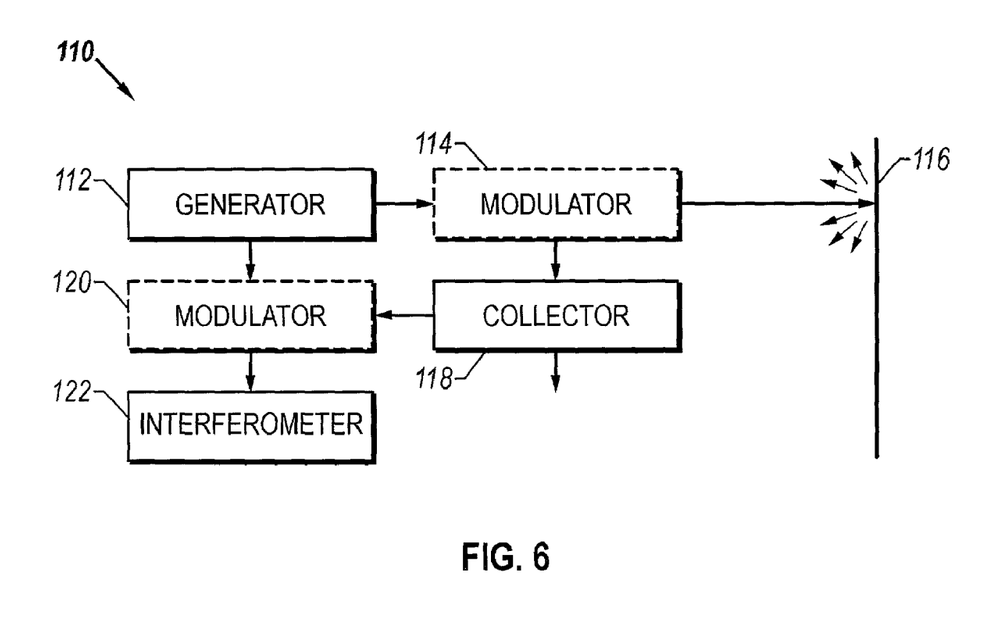
FIG. 6 is a schematic block diagram of an exemplary embodiment of a measuring device as seen in FIG. 1.

FIG. 6 is a schematic block diagram of a exemplary embodiment of a measuring device or detector as seen in FIGS. 1 and 2. The measuring device 110 may have a generator 112, a modulator 114, a collector 118, a modulator 120, and an interferometer. These elements may or may not be included. Further, these elements may be together, separate, or in various combinations, among others.

The generator 112 may generate a coherent electromagnetic energy beam. The beam may or may not be modulated with modulator 114. The beam may be directed to an object 116. A modulated beam may reflect from the object 116 with a characteristic associated with sonic energy waves about the object 116. Part of the modulated beam may be collected in a collector 118. The collected beam may or may not be directed to a modulator 120. The beam may be directed to an interferometer 122 wherein the beam may be detected and measured.

The generator 112 may take various forms. These forms may include a coherent electromagnetic energy source or a laser, among others. Further, the coherent electromagnetic energy source and/or laser may take various forms. These forms may include a $CO_2$ laser, a q-switch YAG laser, a mid-IR laser, an ND:YAG laser and other solid-state and/or gas lasers, among others. However, various lasers may be envisaged.

The modulator 114 may take various forms. These forms may include electro-optic modulators, and acousto-optic modulators, among others. Further, the modulator 114 may alter a characteristic of the beam such as frequency profile, pulse length, phase and pulse amplitude. This function may be performed in conjunction with an amplifier. For example, the modulator 114 may alter the wave characteristic to enhance reflection, compensate for beam attenuation, and compensate for Doppler effects relating to object movement or a scanning motion, among others.

The collector 118 may function to collect part of the reflected modulated beam. The collector may have various apertures.

The modulator 120 may take various forms. These forms may include electro-optic modulators, and acousto-optic modulators, among others. Further, the modulator 114 may alter a characteristic of the beam such as frequency profile, pulse length, phase and pulse amplitude. For example, the modulator 114 may alter the wave characteristic to enhance detection, compensate for beam attenuation, and compensate for Doppler effects relating to object movement or a scanning motion, among others.

The interferometer 122 may take various forms. These forms may include those listed above, among others. These forms may include a Fabry-Perot, dual differential confocal Fabry-Perot, two wave mixing, and photo-refractive interferometer, among others. The interferometer may send a signal relating to the sonic energy wave to an analyzer, control system, or interpreter, among others.

For example, the measuring beam may be generated. The modulator may or may not adjust the beam to provide a preferred frequency profile. The beam may reflect from the wafer with a characteristic associated with the sonic energy signal. The beam may be collected by a collector. The collector may direct the collected beam to an interferometer. In one embodiment, a modulator may or may not adjust the beam.

Figure 7:
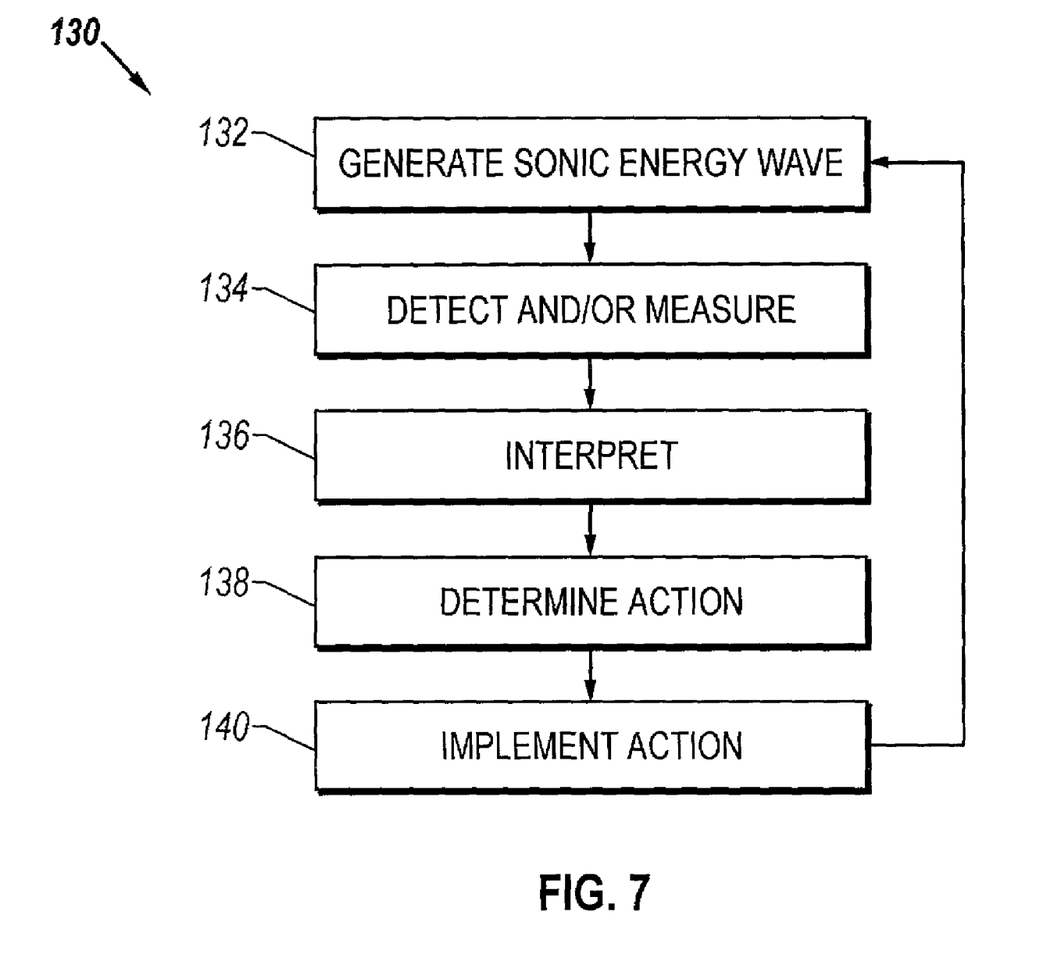
FIG. 7 is a block flow diagram of an exemplary method for use by the system of FIG. 2.

FIG. 7 is a block flow diagram of an exemplary method for use by the system as seen in FIG. 2. In the method 130, a sonic energy wave may be generated about a test object as seen in a block 132. The sonic energy wave may, for example, be generated by directing a beam of coherent electromagnetic energy at the object. However, various means of generating sonic energy waves may be envisaged.

As seen in a block 134, the sonic energy wave may be detected and/or measured by a measuring device. For example, the sonic energy wave may be measured with an interferometer. However, various methods for measuring sonic energy waves may be envisaged.

An interpreter or analyzer may interpret a signal from the measuring device as seen in a block 136. The interpreter or analyzer may use various methods to determine a result. These methods may include regression of parameters from data, determination of the location or amplitude of a peak, and/or comparison of the location or amplitude of the peak to a threshold value, among others. The analysis may be performed on time domain or frequency domain data. In addition, the analysis may utilize generator parameters, object parameters, measurement device parameters, process measurements, and/or process variables, among others.

From the interpretation, a controller or control system may determine an action as seen in a block 138. This action may be to alter a parameter associated with the process. Alternately, the action may relate to the sonic generator, the measurement device, or other process variables. The control system may implement the action as seen in a block 140. In another example, the action may be to alter the frequency of a laser beam to compensate for beam attenuation, Doppler distortion, or noise, among others. In a further example, the action may to alter a characteristic of measuring device. Further, the action may be an alarm or alert. However, various actions may be envisaged.

Figure 8:
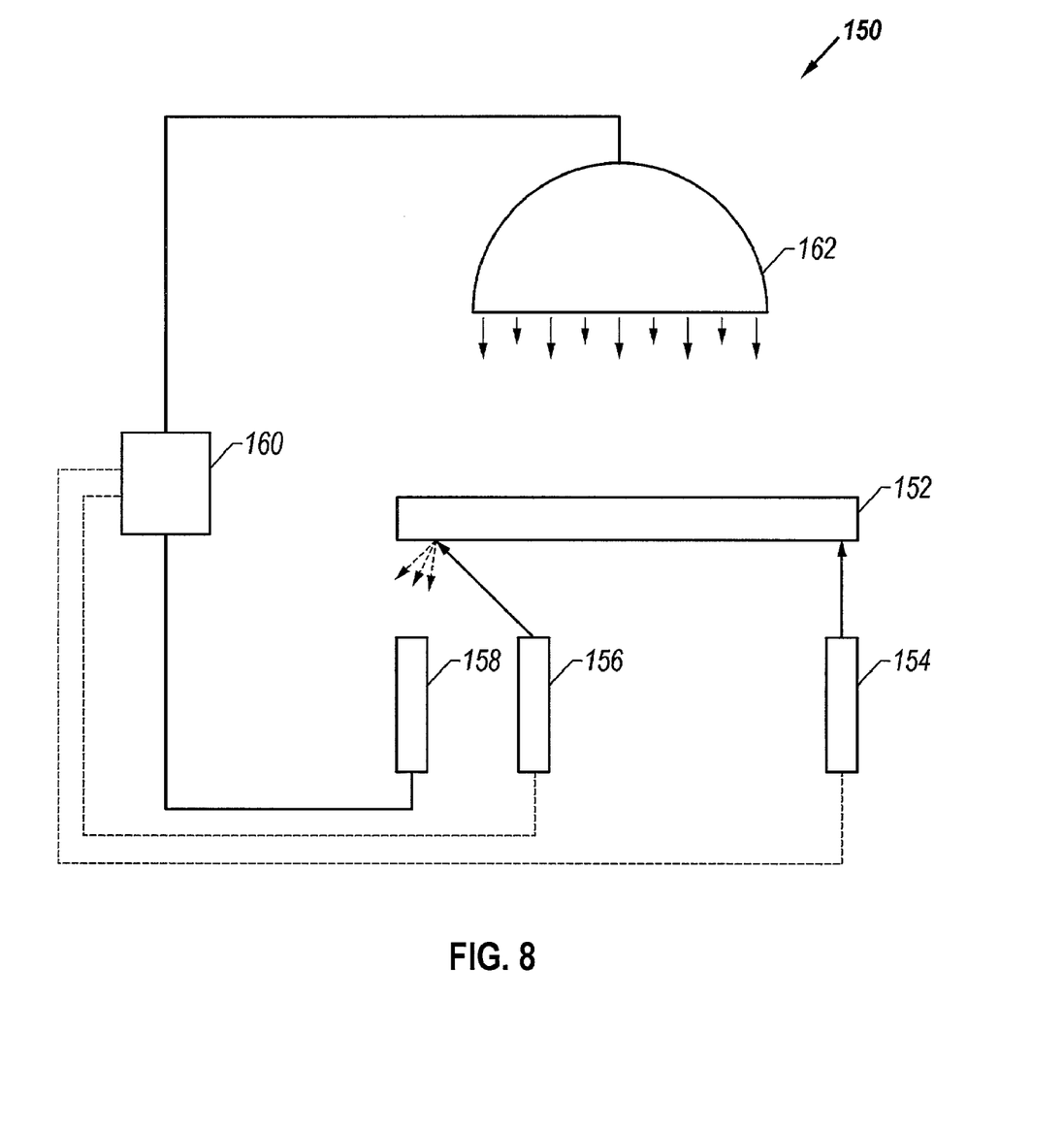
FIG. 8 is a schematic block diagram of an exemplary embodiment of the system as seen in FIGS. 1 and 2.

FIG. 8 is a schematic block diagram depicting an exemplary embodiment of a system as seen in FIGS. 1 and 2. The system 150 has a generating laser 154. The generating laser 154 directs a beam at a semiconductor wafer 152. The beam may impinge a backside of the wafer. Alternately, the beam may impinge the front side of the wafer. The impinging beam may generate a sonic energy signal such as an ultrasonic signal. The system may also have a measuring device. In one exemplary embodiment, the measuring device may have a measuring laser 156 and an interferometer 158. The measuring beam may be directed at the wafer 152 and reflect with a characteristic associated with the sonic energy signal. The interferometer 158 may collect and measure the reflected measuring beam. The interferometer 158 may generate a signal associated with the sonic energy signal.

A control system 160 may receive the signal from the interferometer 158. The control system may determine the temperature of the wafer from the signal. In addition, the control system may determine a control action. For example, the control system 160 may determine the velocity of a sonic energy signal. The temperature may be determined from the velocity and a correlation. Alternately, control system may regress a parameter or use the velocity in determining a control action.

The control action may be to adjust the output of a lamp 162. Alternately, the control system may adjust the behavior or characteristic of the generating laser 154 and/or measuring laser 156. However, various control actions may be envisages.

In addition, more than one measuring device may be utilized. The measuring devices may be directed to the same side or opposite side, among others, of the wafer as the generating laser. For example, each measuring device and the generating laser may be directed at a backside of the wafer. In this manner, the lasers impact the bulk material as opposed to device layers. However, various configurations may be envisaged.

As such, a system and method for process control of semiconductor wafer temperature is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims, which follow.

What is claimed is:

1. An apparatus for determining and implementing a control action associated with a temperature of a semiconductor wafer, the semiconductor wafer associated with a manufacturing process, the apparatus comprising:

a first coherent electromagnetic energy source, the first coherent electromagnetic energy source producing a generator beam of coherent electromagnetic energy, the generator beam of coherent electromagnetic energy impinging the semiconductor wafer and generating a sonic energy signal about the semiconductor wafer;

a second coherent electromagnetic energy source, the second coherent electromagnetic energy source producing a measuring beam of coherent electromagnetic energy, the measuring beam of coherent electromagnetic energy impinging the semiconductor wafer, the measuring beam of coherent electromagnetic energy reflecting from the semiconductor wafer as a scattered electromagnetic energy, the scattered electromagnetic energy having a modulation associated with the sonic energy signal;

an interferometer, the interferometer collecting part of the scattered electromagnetic energy and deriving a signal indicative of the sonic energy signal from the scattered electromagnetic energy;

an analyzer, the analyzer determining a characteristic associated with the temperature of the semiconductor wafer from the signal indicative of the sonic energy signal;

a modulator for manipulating the generation beam based on a sonic energy signal measurement;

a modeler using input comprising process output data to model at least a part of the manufacturing process; and a controller, the controller determining a control action associated with the characteristic associated with the semiconductor wafer, the controller in interactive communication with the modeler.

2. The apparatus of claim 1, wherein the analyzer determines the sonic energy signal velocity by comparing the time domain location of a peak of the sonic energy signal to an expected value and wherein the analyzer estimates wafer temperature from the velocity.

3. The apparatus of claim 1, wherein the modeler further uses an input comprising data selected from the list consisting of a process parameter, a stored result, a threshold value, a process setting, a set point or combinations thereof.

4. A method for determining and implementing a control action associated with a temperature of a semiconductor wafer, the semiconductor wafer associated with a manufacturing process, the method comprising:
producing a generator beam of coherent electromagnetic energy with a first coherent electromagnetic energy source, the generator beam of coherent electromagnetic energy impinging the semiconductor wafer and generating a sonic energy signal about the semiconductor wafer;
producing a measuring beam of coherent electromagnetic energy with a second coherent electromagnetic energy source, the measuring beam of coherent electromagnetic energy impinging the semiconductor wafer, the measuring beam of coherent electromagnetic energy reflecting from the semiconductor wafer as a scattered electromagnetic energy, the scattered electromagnetic energy having a modulation associated with the sonic energy signal;
collecting part of the scattered electromagnetic energy with an interferometer, wherein the interferometer is self stabilized;
deriving a signal indicative of the sonic energy signal from the scattered electromagnetic energy;
determining with an analyzer a characteristic associated with the temperature of the semiconductor wafer from the signal indicative of the sonic energy signal;
manipulating with a modulator the generator beam based on the sonic energy signal measurement;
comparing the signal indicative of the sonic energy signal with an expected value using a comparison algorithm; and
determining with a controller a control action associated with the characteristic associated with the temperature of the semiconductor wafer.

5. The method of claim 4 wherein the characteristic associated with the temperature of the semiconductor wafer is associated with a velocity of the sonic energy signal wherein the sonic energy signal velocity is determined by comparing the time domain location of a peak of the sonic energy signal to an expected value.

6. The method of claim 4 wherein characteristic associated with the temperature of the semiconductor wafer is determined from the sonic energy signal velocity through a regression of data using a propagation model.

7. The method of claim 4, wherein the manufacturing process further comprises a heating lamp directed at the semiconductor wafer, the method further comprising: altering the lamp output.

8. A control system for controlling a temperature associated with a semiconductor wafer in a manufacturing process based on a characteristic associated with a temperature associated with the semiconductor wafer, an interferometer producing a signal associated with a sonic energy signal, the sonic energy signal being associated with the characteristic associated with the temperature associated with the semiconductor wafer, the control system comprising:
an analyzer, the analyzer deriving a temperature of the semiconductor wafer, the analyzer deriving a value from the signal associated with the sonic energy signal;
a modulator for compensating for generation beam attenuation based on a sonic energy signal measurement;
a controller, the controller determining a control action associated with the temperature, the controller implementing the control action on the manufacturing process, and
a modeler, the modeler producing an output.

9. An apparatus for determining and implementing a control action associated with a temperature of a semiconductor wafer, the semiconductor wafer associated with a manufacturing process, the apparatus comprising:
a first coherent electromagnetic energy source, the first coherent electromagnetic energy source producing a generator beam of coherent electromagnetic energy, the generator beam of coherent electromagnetic energy impinging the semiconductor wafer and generating a sonic energy signal about the semiconductor wafer;
a second coherent electromagnetic energy source, the second coherent electromagnetic energy source producing a measuring beam of coherent electromagnetic energy, the measuring beam of coherent electromagnetic energy impinging the semiconductor wafer, the measuring beam of coherent electromagnetic energy reflecting from the semiconductor wafer as scattered electromagnetic energy, the scattered electromagnetic energy having a modulation associated with the sonic energy signal;
an interferometer, the interferometer collecting part of the scattered electromagnetic energy and deriving a signal indicative of the sonic energy signal from the scattered electromagnetic energy, wherein the interferometer is self-stabilized;
a modulator altering the generator beam attenuation based on measuring the sonic energy signal;
an analyzer, the analyzer determining the temperature of the semiconductor wafer from the signal indicative of the sonic energy signal by subtracting an expected result from a peak amplitude of the signal; and
a controller, the controller determining a control action associated with the temperature of the semiconductor wafer.

10. A method for determining and implementing a control action associated with a temperature of a semiconductor wafer, the semiconductor wafer associated with a manufacturing process, the method comprising:
producing a generator beam of coherent electromagnetic energy with a first coherent electromagnetic energy source, the generator beam of coherent electromagnetic energy impinging the semiconductor wafer and generating a sonic energy signal about the semiconductor wafer;
producing a measuring beam of coherent electromagnetic energy with a second coherent electromagnetic energy source, the measuring beam of coherent electromagnetic energy impinging the semiconductor wafer, the measuring beam of coherent electromagnetic energy reflecting from the semiconductor wafer as a scattered electromagnetic energy, the scattered electromagnetic energy having a modulation associated with the sonic energy signal;
collecting part of the scattered electromagnetic energy with an interferometer;
deriving a signal indicative of the sonic energy signal from the scattered electromagnetic energy, wherein the signal is derived using a self-stabilized interferometer;
determining the temperature of the semiconductor wafer from the signal indicative of the sonic energy signal;

determining with a controller a control action associated based on the temperature of the semiconductor wafer; and manipulating with a modulator, the generator beam, based on the sonic energy signal measurement.

11. The system of claim 1, wherein the modeler is a propagation model and the analyzer is adapted to regress a parameter associated with a semiconductor wafer temperature by utilizing the propagation model.

12. The method of claim 4, further comprising adjusting the generator beam frequency to compensate for attenuation in the semi-conductor wafer.

13. The method of claim 10, further comprising modeling with process results stored from a previous manufacturing process, and implementing an optimal control action based on the step of modeling the control action.

* * * * *

UNITED STATES PATENT AND TRADEMARK OFFICE
CERTIFICATE OF CORRECTION

| | | |
|---|---|---|
| PATENT NO. | : 7,612,890 B2 | Page 1 of 1 |
| APPLICATION NO. | : 10/142178 | |
| DATED | : November 3, 2009 | |
| INVENTOR(S) | : Thomas E. Drake, Jr. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 558 days.

Signed and Sealed this

Nineteenth Day of October, 2010

David J. Kappos
*Director of the United States Patent and Trademark Office*